(12) United States Patent
Bolz

(10) Patent No.: US 10,220,138 B2
(45) Date of Patent: Mar. 5, 2019

(54) THROUGH-FLOW REGULATING DEVICE FOR A HOSE LINE OF A MEDICAL INFUSION SYSTEM

(71) Applicant: B. BRAUN MELSUNGEN AG, Melsungen (DE)

(72) Inventor: Johannes Bolz, Kassel (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 0 days.

(21) Appl. No.: 15/596,475

(22) Filed: May 16, 2017

(65) Prior Publication Data

US 2017/0333627 A1   Nov. 23, 2017

(30) Foreign Application Priority Data

May 19, 2016   (DE) .......................... 10 2016 208 677

(51) Int. Cl.
  *A61M 5/168* (2006.01)
  *A61M 39/28* (2006.01)
  *F16K 7/06* (2006.01)

(52) U.S. Cl.
  CPC ...... *A61M 5/16813* (2013.01); *A61M 39/284* (2013.01); *A61M 39/285* (2013.01); *F16K 7/065* (2013.01)

(58) Field of Classification Search
  USPC .......................................................... 251/6
  See application file for complete search history.

(56) References Cited

U.S. PATENT DOCUMENTS

| 788,553 | A | * | 5/1905 | Nicolaus | ................ B65D 43/18 220/822 |
|---|---|---|---|---|---|
| 2,112,592 | A | * | 3/1938 | MacClatchie | ............. F16K 7/06 251/4 |
| 2,681,751 | A | * | 6/1954 | Weber | ...................... A47K 5/10 137/630.2 |
| 3,279,656 | A | * | 10/1966 | Axtell | .................. B65D 77/067 222/105 |

(Continued)

FOREIGN PATENT DOCUMENTS

| CN | 201067582 Y | 6/2008 |
|---|---|---|
| CN | 202376557 U | 8/2012 |

(Continued)

OTHER PUBLICATIONS

European Search Report for European Application No. 17170354.9, dated Sep. 5, 2017, with partial translation, 9 pages.

*Primary Examiner* — Robert K Arundale
*Assistant Examiner* — Daphne M Barry
(74) *Attorney, Agent, or Firm* — RatnerPrestia

(57) ABSTRACT

A through-flow regulating device for a hose line of a medical infusion system having at least one rotationally movable clamping member which, in the mounted state, is operatively connected to the hose line and which can be manually adjusted relative to a hose section of the hose line in order to change a fluid through-flow rate of the hose section. Two clamping members mounted in a rotationally movable manner are provided, which flank a jacket of the hose section on opposite sides, and at least one clamping member has a circumferential contour which is formed, at least in sections, in an eccentric manner relative to an axis of rotation of the clamping member.

18 Claims, 7 Drawing Sheets

(56) References Cited

U.S. PATENT DOCUMENTS

| | | | | |
|---|---|---|---|---|
| 4,114,640 A | * | 9/1978 | Forman | A61F 5/4407 |
| | | | | 137/381 |
| 4,634,421 A | * | 1/1987 | Hegemann | A61F 2/0009 |
| | | | | 251/7 |
| 4,660,802 A | | 4/1987 | Oscarsson | |
| 4,682,755 A | * | 7/1987 | Bernstein | F16K 7/07 |
| | | | | 251/252 |
| 5,320,256 A | * | 6/1994 | Wood | B65D 47/2037 |
| | | | | 222/212 |
| 5,352,214 A | | 10/1994 | Oscarsson | |
| 5,494,189 A | * | 2/1996 | De Crane | B65B 69/0091 |
| | | | | 222/1 |
| 6,079,628 A | * | 6/2000 | Kenny | G05D 16/0619 |
| | | | | 236/93 R |
| 7,322,556 B2 | * | 1/2008 | Bernstein | F16K 7/063 |
| | | | | 251/4 |
| 8,544,815 B2 | | 10/2013 | Avery et al. | |
| 2005/0283165 A1 | * | 12/2005 | Gadberry | A61M 39/0613 |
| | | | | 606/108 |
| 2013/0110087 A1 | * | 5/2013 | Kane | A61M 25/00 |
| | | | | 604/543 |

FOREIGN PATENT DOCUMENTS

| | | |
|---|---|---|
| DE | 102014213576 A1 | 1/2016 |
| EP | 1452202 A1 | 9/2004 |
| GB | 646167 | 11/1950 |
| GB | 1212781 | 1/1968 |

\* cited by examiner

THROUGH-FLOW REGULATING DEVICE FOR A HOSE LINE OF A MEDICAL INFUSION SYSTEM

CROSS REFERENCE TO RELATED APPLICATIONS

This application claims priority to German application DE 10 2016 208 677.4 filed May 19, 2016, the contents of such application being incorporated by reference herein.

FIELD OF THE INVENTION

The invention relates to a through-flow regulating device for a hose line of a medical infusion system, having at least one rotationally movable clamping member which, in the mounted state, is operatively connected to the hose line and which can be manually adjusted relative to a hose section of the hose line in order to change a fluid through-flow rate of the hose section.

DESCRIPTION OF THE RELATED ART

U.S. Pat. No. 8,544,815 B2 discloses a through-flow regulating device for a hose line of a medical infusion system. The through-flow regulating device has a housing in which a channel passage for a hose section of the hose line is provided. A clamping segment is assigned to the channel passage, which clamping segment is adapted to the channel passage in an arc-shaped manner and allows compression over a large area of the hose section situated in the channel passage. A displacement of the clamping segment takes place by means of an eccentric mounted in a rotationally movable manner in the housing. The eccentric is rotated via an adjustment wheel which is mounted on the outside of the housing. In order to displace the clamping segment between an open position and a closed position in which the hose section is pressed together for a blocked position, the adjustment wheel must be rotated through at least 180°.

SUMMARY OF THE INVENTION

An object of the invention is to provide a through-flow regulating device of the type initially mentioned, which can be produced with little effort and can be operated in a simple manner and also allows an accurate settability of a drop rate.

Said object is achieved in that two clamping members mounted in a rotationally movable manner are provided, between which the hose section is passed through and which flank a jacket of the hose section on opposite sides with their circumferential contours, and in that the circumferential contour of at least one clamping member is formed, at least in sections, in an eccentric manner relative to an axis of rotation of the clamping member. Advantageously, the two clamping members are of at least substantially cylindrical design and flank the jacket of the hose section with their circumferential contours in a substantially tangential manner, wherein at least one of the clamping members is provided with the eccentric circumferential contour. By virtue of the fact that the respective hose section is extended between two clamping members, symmetric compression of the hose section from opposite sides is made possible. This results in an improved settability of a through-flow rate of the hose line and therefore of a drop rate. Moreover, the jacket of the hose section is deformed in a uniform manner and to a relatively small extent compared to one-sided loading. The solution according to aspects of the invention allows a linear compression of the hose section, since the hose section is passed through between opposite curvature peaks of the two clamping members in the manner of a tangent. The invention can be advantageously used for gravity-driven infusion systems.

In a configuration of the invention, the two clamping members are mounted in a rotationally movable manner, such that they move synchronously in opposite directions to one another, using a synchronizing device. The oppositely-positioned clamping members preferably roll in opposite directions to one another via their synchronizing device. A toothing gear mechanism is preferably provided as a synchronizing device, wherein a complementary toothing section is respectively assigned to each clamping member. The toothing sections are preferably arranged co-axially relative to the axes of rotation of the clamping members.

In a further configuration of the invention, an eccentric clamping section of the circumferential contour is of concave design with a radial and an axial supporting wall region, which regions act upon the hose section on the jacket side relative to an axis of rotation of the clamping member in dependence on a rotation of the clamping member. The terms "radial" and "axial" refer to the axis of rotation of the clamping member and mean that the corresponding hose section, as seen in cross section, is enclosed in an approximately right-angled manner, in order to prevent an escape of the hose section in the axial direction of the axis of rotation of the clamping member and in the radial direction of the axis of rotation of the clamping member.

In a further configuration of the invention, in the circumferential direction of the clamping section, a spacing of the radial supporting wall region relative to the axis of rotation of the clamping member changes in a continuous or discontinuous manner over a length of the supporting wall region. The change of the spacing of the radial supporting wall region relative to the axis of rotation—as seen in the circumferential direction—exerts necessarily changing loads on the jacket of the hose section during a rotation of the clamping member and of the clamping section about the axis of rotation, as a consequence of which—depending on the direction of rotation—a reduction or increase of the through-flow rate of a fluid passed through the hose line results. Continuous or discontinuous change is to be understood as a non-stepped or a stepped change. The spacing in the direction of rotation, that is to say in the circumferential direction, preferably changes in a stepless manner during a rotation, in order to achieve a non-stepped increase or reduction of the compressive pressure on the hose section.

In a further configuration of the invention, both clamping members are provided with eccentric clamping sections which are complementary to one another. The eccentric clamping sections of the two clamping members are preferably of a design that is mirror symmetric along a diagonal of a cross section of the hose section. Consequently, transversely to its longitudinal extent, the jacket of the hose section is held securely on all sides between the eccentric clamping sections. The eccentric clamping sections of both clamping members are preferably provided with identical radial and axial supporting wall regions, which regions are diagonally opposite one another relative to the hose section. The supporting wall regions of the two clamping sections therefore form a positively locking support of the hose section in all directions transverse to the longitudinal extent thereof. The oppositely-positioned clamping sections of the two clamping members effect a linear compression on the hose section in a radial plane of the hose section—relative to the longitudinal axis of said section. The eccentric clamping sections in developed view are advantageously of mirror-symmetric design relative to a diagonal plane 35 (see FIG. 2).

In a further configuration of the invention, the two clamping members are oriented relative to the hose section in such a manner that clamping forces of the clamping members acting on the hose section lie in a common radial plane of both axes of rotation of the clamping members. The radial plane accommodates both axes of rotation of the clamping members. Oppositely-directed pressure forces of the loaded hose section therefore also act in the direction of respectively one axis of rotation. Forces generated by the compression of the hose section on opposite sides act in the direction of both axes of rotation. This ensures that a through-flow rate, once set, does not change independently. Maximum compression occurs—as seen in top view—along a connecting line of the two axes of rotation. A linear contact of the circumferential contours of the two clamping sections of the clamping members on the jacket of the hose section leads, in the case of an incomplete through-flow blocking, to a central pressing-together occurring in the longitudinal direction of the hose section, as a consequence of which, in the case of an incomplete pressing-together, two fluid channels above and below the linear compression result. The free cross sections of said resulting two fluid channels can be varied relative to one another by rotating the clamping members.

In a further configuration of the invention, the synchronizing device has two circular-arc-shaped toothing sections, which mesh with one another and are each assigned to a clamping member. The toothing sections are oriented co-axially relative to the respective axis of rotation. The toothing sections are designed in an identical manner with respect to one another, in order to effect a play-free meshing in the manner of two toothed wheels. The toothing sections preferably extend in each case over a circular arc, which covers an angle of at most 90°.

In a further configuration of the invention, the toothing sections are provided in one piece on the clamping members. Here, in each case, a toothing section is assigned to the associated clamping member. The two clamping members are preferably produced from plastic and the toothing sections are moulded in one piece onto the clamping members.

In a further configuration of the invention, an adjustment angle of each clamping member between an open position, in which it opens up the hose section for a full fluid through-flow, and a blocked position, in which it closes the hose section for a fluid through-flow, is less than or equal to 90°. This relatively small adjustment travel allows an extremely simple and ergonomically convenient manual operation. With a handle, an adjustment between the open position and the blocked position can be performed. An angle covered by the respective circular-arc-shaped toothing section is preferably also at most 90°. In the case of one-piece moulding of the respective toothing section onto the respective clamping member, the adjustment angle of the clamping member and the covered angle of the respective toothing section are necessarily identical.

In a further configuration of the invention, the two clamping members are mounted and held relative to one another. The two clamping members are either directly connected to one another and thus mounted and held relative to one another, or they are rotatably mounted in a carrier housing which preferably is likewise produced from plastic.

In a further configuration of the invention, the carrier housing is constructed from a base shell and a cover shell between which the clamping members are arranged, wherein the base shell and the cover shell are connected to one another in the region of the axes of rotation. This results in a particularly simple producibility of the through-flow regulating device. The through-flow regulating device can be assembled from a few plastic components. The base shell and the cover shell can be formed as identical parts.

In a further configuration of the invention, the two clamping members are formed as identical parts. As a result of this, a further simplification of the production and thus a cost reduction is achieved.

In a further configuration of the invention, each clamping member has at least one operating lever which projects outwardly relative to the axis of rotation, opposite to the eccentric clamping section. The respective operating lever is oppositely-positioned in such a manner that, relative to the axis of rotation, it effects a lever arm for the rotation of the eccentric clamping section. In a particularly advantageous manner, the operating lever is moulded in one piece on the clamping member. The operating lever advantageously projects in a wing-like manner, such that the operating levers of the two clamping members project outwardly in the manner of wing legs and can be manually operated together.

In a further configuration of the invention, each clamping member has two operating levers which project in the manner of a rocker in different directions relative to the axis of rotation. All operating levers project outwardly in the plane of rotation of the respective clamping member. The rocker-type orientation ensures that at least one operating lever of each clamping member is always easily accessible to the operating person for manual operation, regardless of the position of the respective clamping member.

In a further configuration of the invention, the at least one operating lever projects laterally outwards beyond the carrier housing at least in sections. As a result of this, the manual operability of the through-flow regulating device is further improved. Due to the fact that the at least one operating lever projects laterally outwards, the at least one operating lever is always clearly visible to an operator and can be operated in an ergonomically simple manner.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
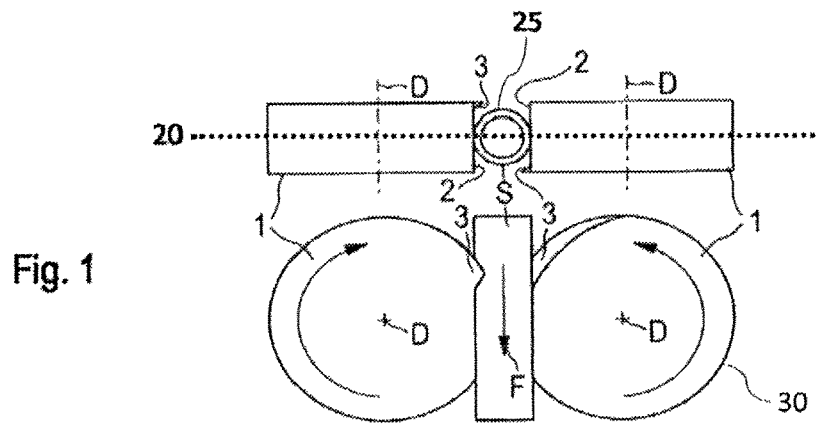
FIGS. 1, 2, and 3 show, in different positions, a schematic functioning principle of an embodiment of a through-flow regulating device according to aspects of the invention.

A through-flow regulating device, as represented on the basis of FIGS. 1 to 15, is provided for the use of a hose line of a medical infusion system, wherein the infusion system is gravity-driven. The hose line serves to feed a fluid from a fluid storage unit to a catheter, which can be fastened on the patient side. The hose line is formed in a flexible manner and has a hose section S which, in the mounted state, extends within the through-flow regulating device according to FIGS. 1 to 15. The hose section S can, using the through-flow regulating device, be acted upon in a stepless manner from an open position, in which a free cross section of the hose section S is not subjected to load, to a blocked position, in which the hose section is completely pressed together from opposite sides. A through-flow rate of the fluid flowing through the hose section S can thereby be set. The hose section S of the hose line is passed through between two clamping members 1, mounted in a rotationally movable manner, of the through-flow regulating device, which members are rotatably mounted, in each case about an axis of rotation D, relative to one another or relative to a carrier housing. The two axes of rotation D are oriented parallel to one another. According to the schematic embodiment in FIGS. 1 to 3, the two clamping members 1 are designed as rotatable cylinder bodies which flank the hose section S on opposite sides. The two clamping members 1 are rotatably mounted in a common plane in which also the hose section S is extended. Said common plane forms a common radial plane 20 of the two axes of rotation D. The two clamping members 1 have in each case a circumferential contour 40 in the region of their circumferential edge 30 which has in each case an eccentric clamping section 2, 3 over a partial region of their circumference, the spacing of which section relative to the respective axis of rotation D changes continuously over the length of the clamping section, as seen in the circumferential direction. The two clamping members 1 with their eccentric clamping sections 2, 3 are formed in an identical manner with respect to one another, wherein, however, the one clamping member 1 is oriented in a manner rotated through 180° relative to the other clamping member 1. The axes of rotation D of the two cylinder-like clamping members 1 lie—as seen in top view—on a connecting line, which line intersects a longitudinal direction of the hose section S (indicated by a fluid through-flow direction F) in an orthogonal manner. Corresponding forces of the contact contours of the eccentric clamping sections 2, 3 in the region of said connecting line thereby also act on correspondingly opposite jacket 25 outer surfaces of the hose section S. Restoring forces of the hose section S, which are generated by elastic deformation forces while the hose section S is being pressed together, therefore act along this imaginary connecting line exactly in the direction of the axes of rotation D.

The corresponding contact contours of the two eccentric clamping sections of the oppositely-positioned clamping members 1 have both radial supporting wall regions 2 and axial supporting wall regions 3. The radial and axial supporting wall regions merge into one another in a continuously conical and/or concave manner, as seen in developed view over the length of the circumferential contour of the respective clamping member 1. It is essential that the corresponding contact contours, even in the case of inclined, conical, concave or convex curvature, always form axial and radial supporting components which act on the hose section S.

Figure 2:
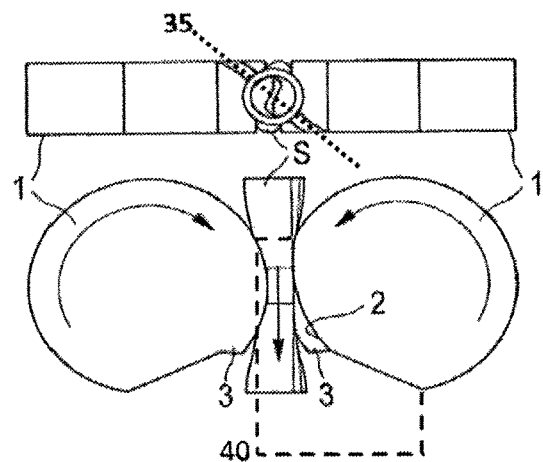

It will be seen from FIG. 2 that the oppositely-positioned contact contours of the two eccentric clamping sections of the clamping members 1 are positioned mirror-symmetrically opposite to one another relative to a diagonal 35 in such a manner that, in certain squeezing positions of the hose section S, they effect central linear contacts of an inner side of the jacket 25 of the hose section S, as a consequence of which two fluid channel sections of the hose section S that are separate from one another form above and below these linear contacts. In case of a completely pressed-together hose section S, a fluid through-flow is completely blocked, as can be seen from FIG. 3. In this position, the eccentric clamping sections of the clamping members 1 no longer have any effective axial supporting wall regions. Instead, the corresponding contact contours are exclusively intended for the radial support, as can be seen from FIG. 3.

In order to ensure that the two clamping members 1 are always rotated synchronously and in opposite directions to one another, the through-flow regulating device additionally has a synchronizing device which acts on the two clamping members 1. Said synchronizing device is not illustrated in FIGS. 1 to 3.

In the practical embodiment according to FIGS. 4 to 15, however, the synchronizing device is shown. Said device is formed by corresponding toothing segments 11 which are moulded onto the respective clamping member 4 and are oriented co-axially relative to the respective axis of rotation 6 of the clamping member 4. The toothing segments 11 extend in a circular-arc-shaped manner through an angle of approximately 90° relative to the axis of rotation 6. The toothing segments 11 of the neighbouring clamping members 4 mesh with one another.

It will be seen from FIGS. 4 to 15 that each clamping member 4 is formed as a one-piece plastic component which is rotatably mounted about the respective axis of rotation 6. The functioning principle of the through-flow regulating device according to FIGS. 4 to 15 corresponds to the above-described functioning principle according to FIGS. 1 to 3. The axes of rotation 6 therefore correspond in a functional sense to the axes of rotation D, the clamping members 4 correspond to the clamping members 1 according to FIGS. 1 to 3, and corresponding eccentric clamping sections 10 correspond to the eccentric clamping sections 2, 3, as already described on the basis of FIGS. 1 to 3. In the following text, only the embodiment according to FIGS. 4 to 15 will be addressed. Each clamping member 4 forms a clamping body which, on an inner side facing the opposite clamping member 4, is provided with the eccentric clamping section 10 with corresponding contact contours for the hose section to be squeezed. The contact contours of the eccentric clamping sections 10 can be seen from FIGS. 5 to 7. The eccentric clamping sections 10 extend—as also the toothing segments 11—over a circumferential angle of approximately 90° relative to the respective axis of rotation 6. The eccentric clamping sections 10 are provided between the edge-side toothing segments 11. It will be seen from FIGS. 5 to 7 that each clamping member 4 is formed as a one-part shell component which, in the region of its oppositely-positioned side walls, is provided on the edge side with in each case one toothing segment 11, such that the two clamping members 4 mesh with one another via in total four toothing segments 11. Between the lateral toothing segments 11, the eccentric clamping section 10 of the respective clamping member 4 is provided in each case. The two clamping members 4 are formed in an identical manner with respect to one another, but positioned in a manner rotated through 180° relative to one another. The two clamping members 4 therefore form identical parts. The two clamping members 4 are rotatably mounted with their axes of rotation 6 in a carrier housing, which housing forms a base shell and a cover shell 5 which are likewise formed as identical parts. The base shell and the cover shell 5 are provided with a gripping handle 9 that is moulded in one piece. The two housing shells 5 of the carrier housing are connected to one another via corresponding plug elements in the region of the two axes of rotation 6. The plug elements are designed on the one hand as locking elements for securing the two housing shells 5 with respect to one another and on the other hand as axes of rotation for the clamping members 4, which members form correspondingly complementary bearing receptacles. At least one plug element of each axis of rotation 6 is designed as a plug pin, in order to allow assembly and if appropriate disassembly of the housing shells 5 and the clamping members 4 relative to one another. The plug pin can be moulded in one piece on the cover shell or the base shell.

Figure 5:
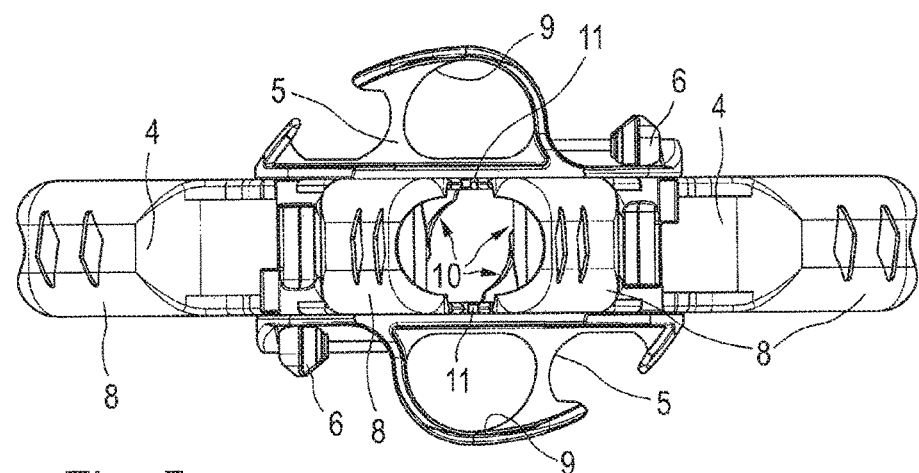
Figure 6:
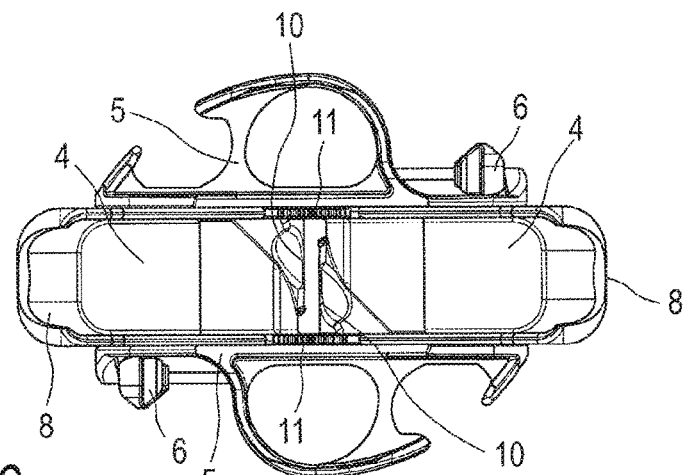
Figure 7:
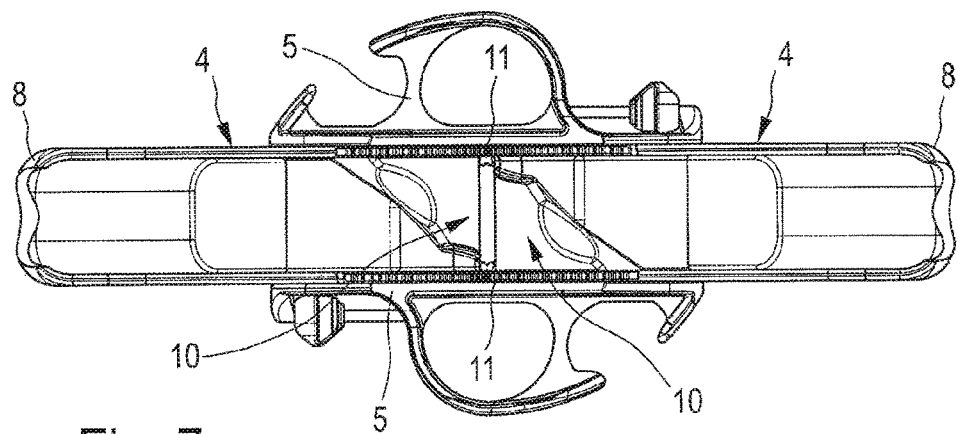
Figure 8:
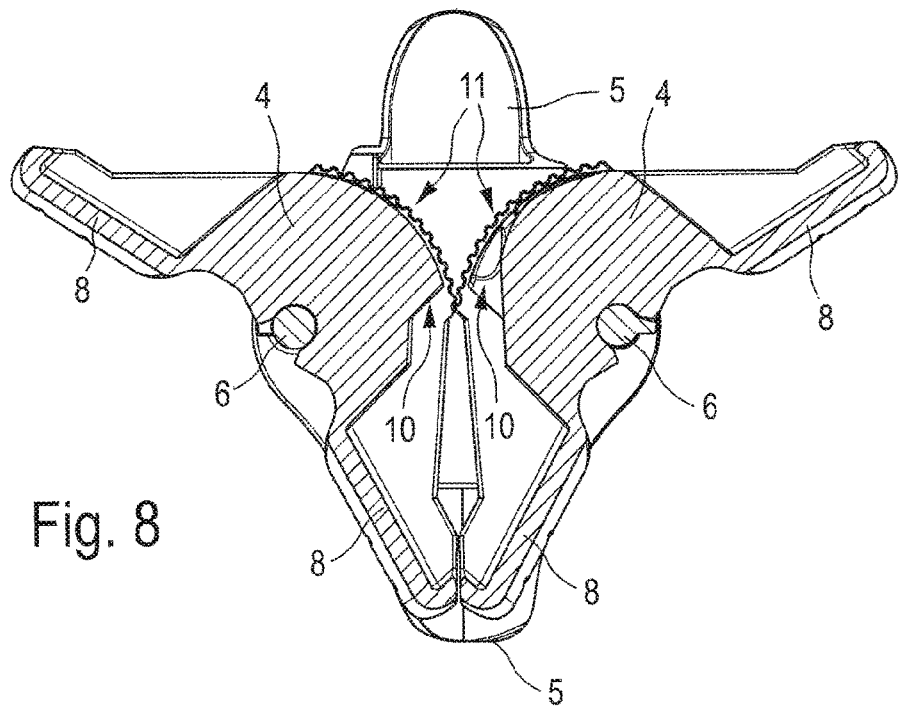
FIGS. 8, 9, 10, and 11 show, in longitudinal section views, the through-flow regulating device according to FIGS. 4 to 7 in the different actuating positions
Figure 9:
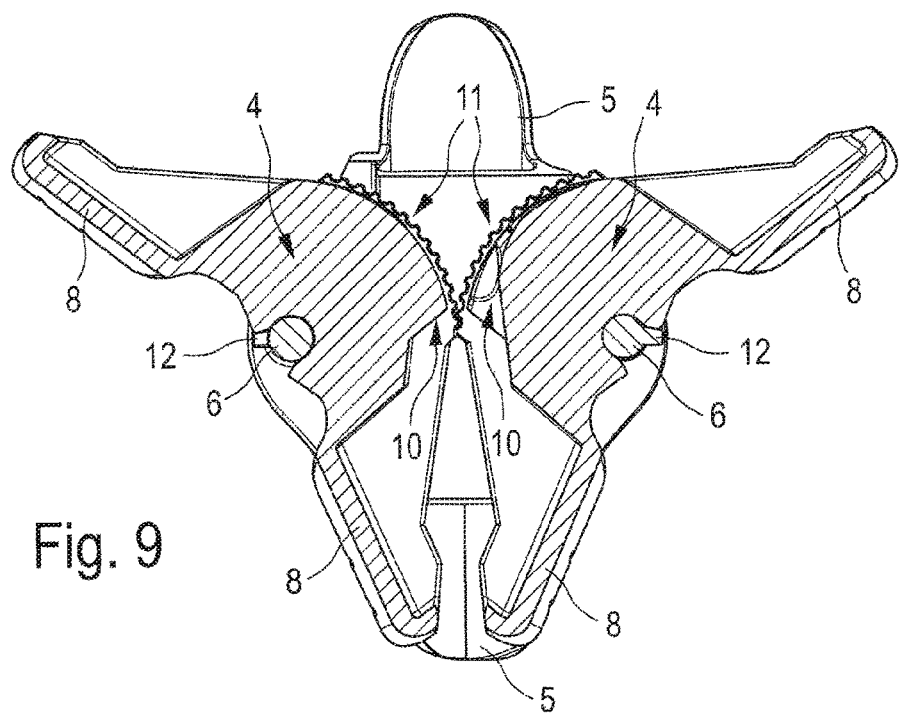
Figure 10:
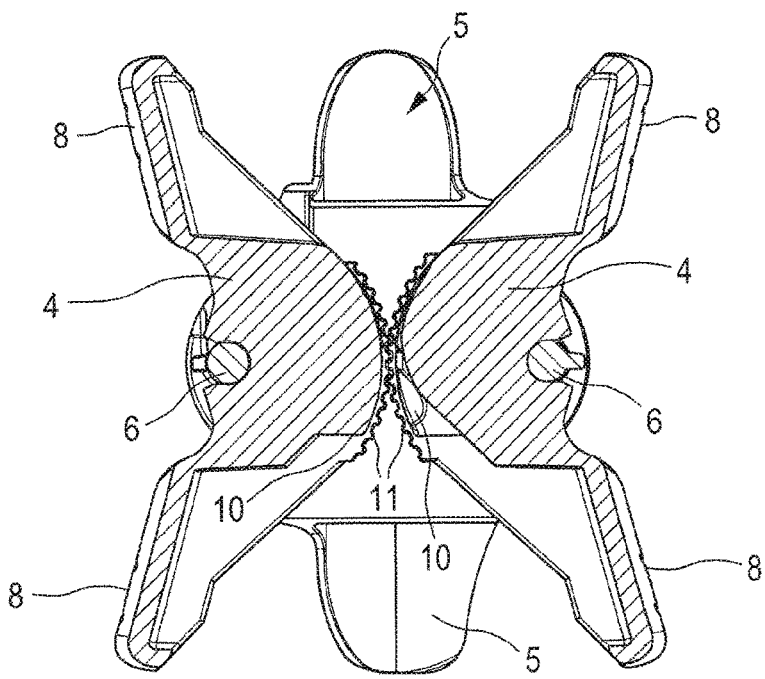
Figure 11:
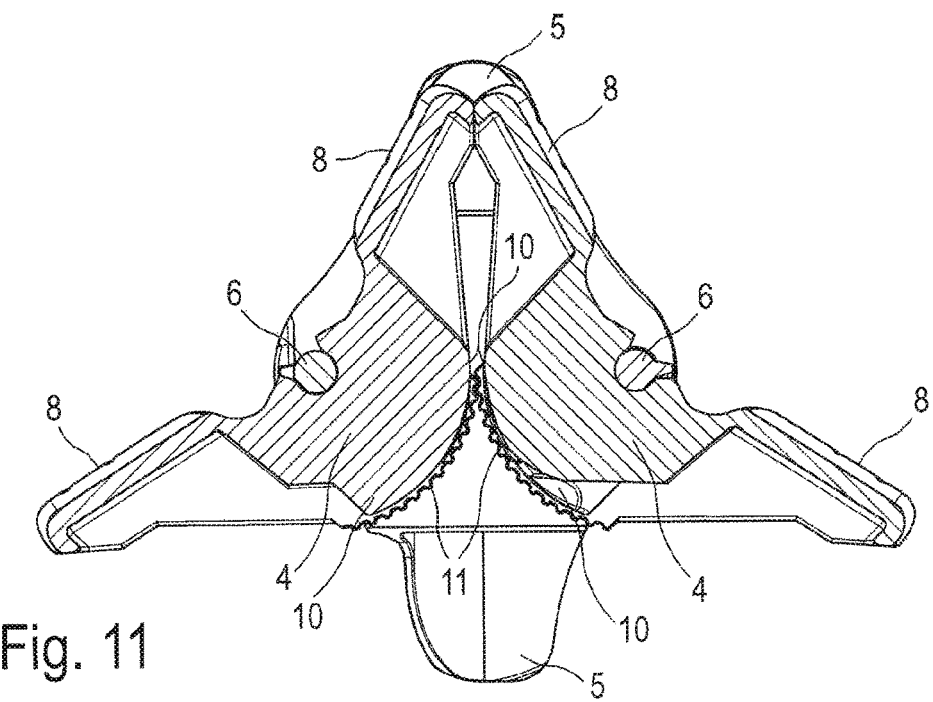
Figure 12:
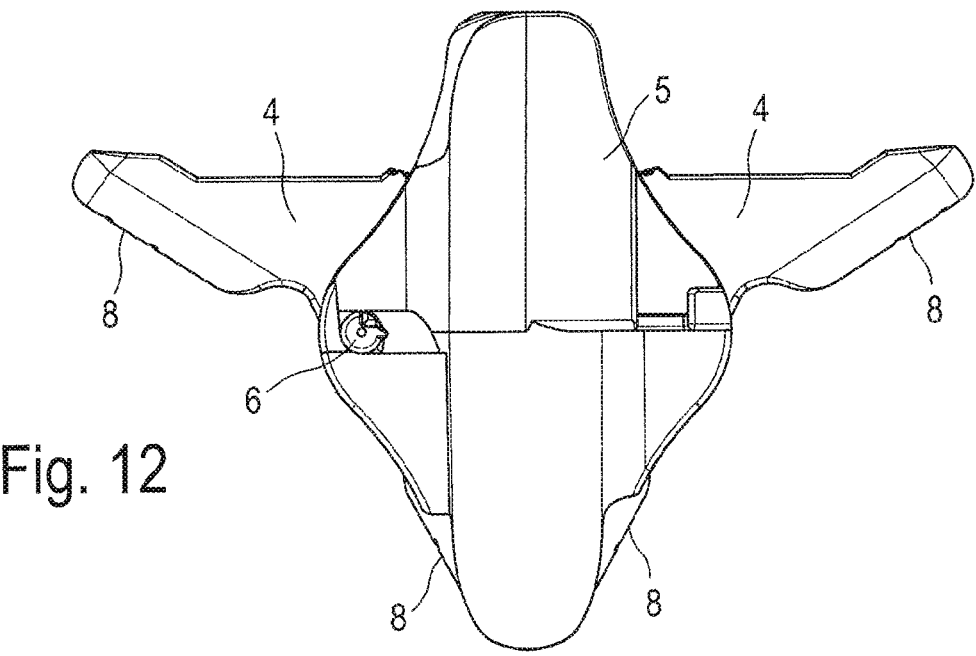
FIGS. 12, 13, 14, and 15 show, in each case in top view, the through-flow regulating device according to FIGS. 4 to 11 in the different actuating positions, analogously to FIGS. 8 to 11.
Figure 13:
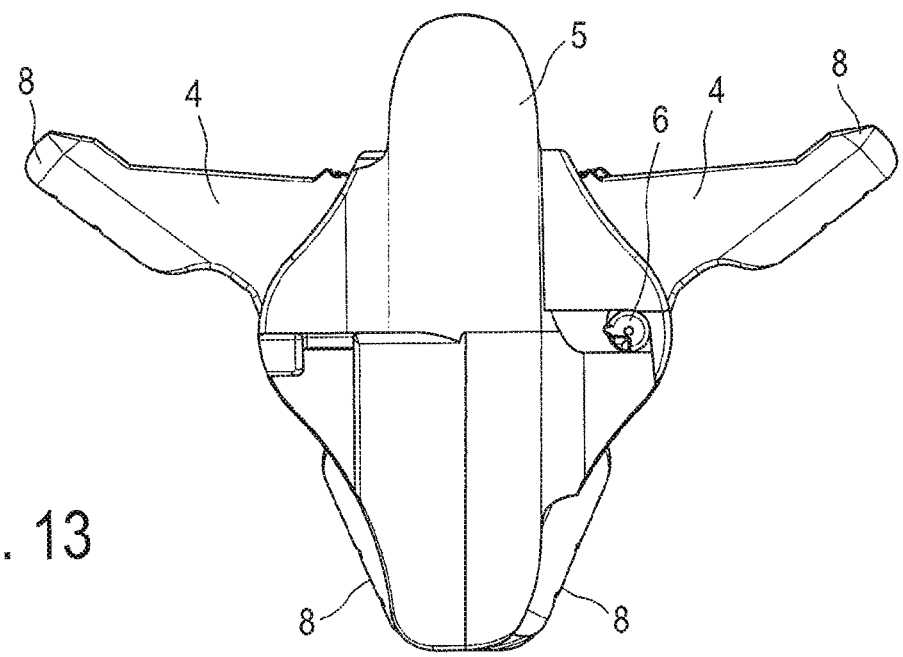
Figure 14:
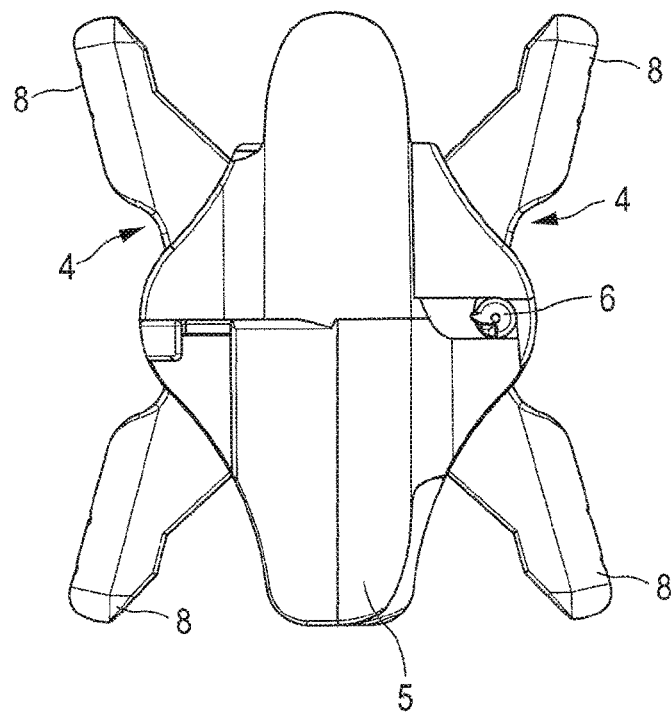
Figure 15:
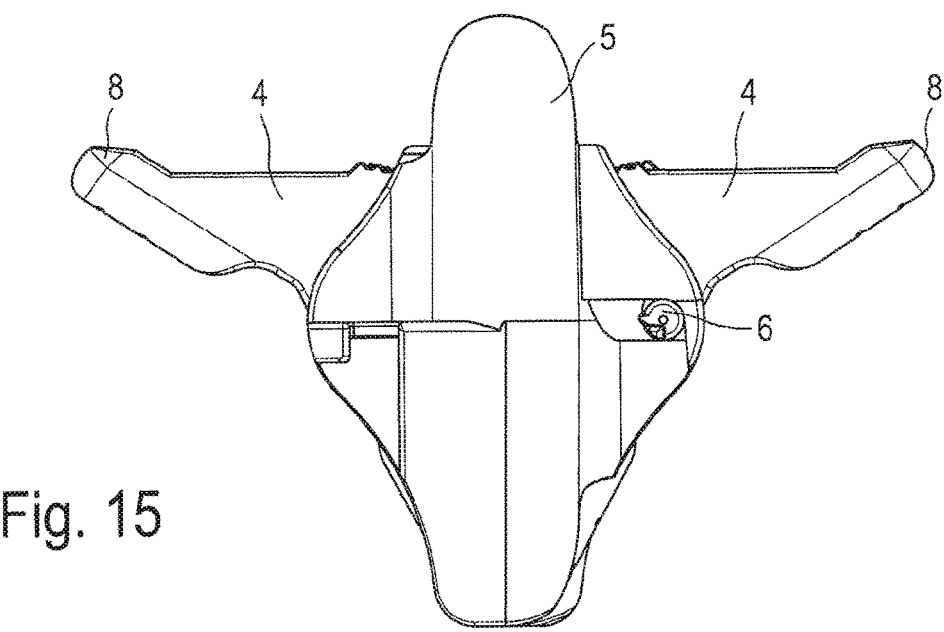

It will be seen from FIGS. 8 to 11 that the axes of rotation 6 are provided with stops 12 which limit the rotational mobility of the respective clamping member 4 to an angle of approximately 90°. The bearing receptacles of the clamping members 4 have corresponding complementary stops, in order to ensure the limited rotational mobility. Each clamping member 4 has two wing-shaped operating levers 8 which are moulded in one piece on the clamping body and project towards oppositely-positioned sides relative to the axis of rotation 6. Also, the wing-shaped operating levers 8 are arranged in the radial plane 20 in which the respective clamping member 4 extends. The wing-shaped operating levers 8 project, relative to the respective eccentric clamping section 10, from the axis of rotation 6 towards oppositely-positioned sides, in order, in the case of a manual actuation, to form corresponding lever arms for a rotation of the respective clamping lever 4. FIGS. 8 to 11 indicate the maximum setting travel of the two clamping members 4. In FIG. 8, a mounting position for mounting the through-flow regulating device on a corresponding hose line is illustrated. In FIG. 9, a largely open position of the through-flow regulating device according to FIG. 5 is shown, in FIG. 10 a largely closed position corresponding to FIG. 6 is shown, and in FIG. 11 a completely closed position according to FIG. 7 is shown. FIGS. 12 to 15 show the through-flow regulating device according to FIGS. 8 to 11 in top view, in respectively analogous function positions, wherein FIG. 12 shows an orientation that is rotated in the drawing plane through 180° compared to the illustration in FIG. 13.

Figure 3:
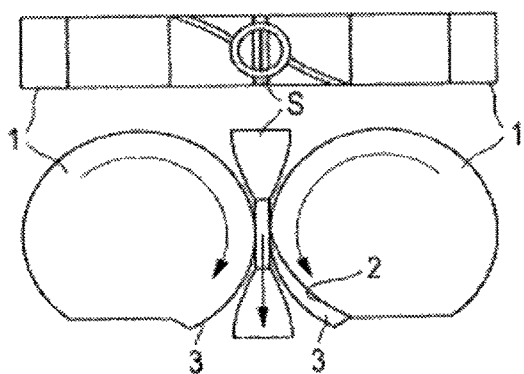
Figure 4:
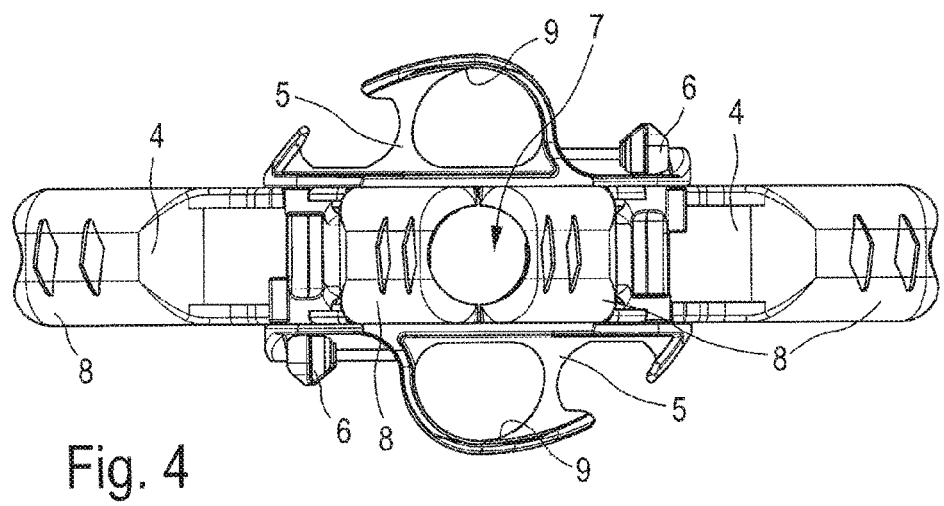
FIGS. 4, 5, 6, and 7 show, in front view, a practical embodiment of a through-flow regulating device according to aspects of the invention in different actuating positions.

It will be seen from FIGS. 8 to 15 that the two clamping members 4 are, relative to a longitudinal extent of a hose section S, which is shown only in FIGS. 1 to 3, mirror-symmetrically adjustable such that they move synchronously and in opposite directions to one another. It will be seen from FIGS. 8 to 15 that at all times at least two wing-shaped operating levers 8 of the clamping members 4 project laterally beyond outside edge contours of the housing shells 5, such that at least one operating lever 8 can be gripped and operated in a simple manner. An operating person preferably reaches into the gripping handle 9 of a housing shell 5 with the finger of one hand and pushes one of the wing-shaped operating levers 8 in a correspondingly desired direction of rotation with another finger, preferably with the thumb. As a result, a corresponding through-flow rate of the hose section S is necessarily changed. Since the total adjustment angle of the two clamping members 4 is, in total, only approximately 90°, the operating person does not have to change grip in order to completely block the hose line from a completely open position. In addition, the operation is equally suitable for right-handed and left-handed persons.

The plug elements in the region of the axes of rotation 6 and also the clamping members 4 and the housing shells 5 are formed in such a manner that the individual components can be assembled to form the operational structural unit without tools, which unit is the through-flow regulating device illustrated in FIGS. 4 to 15. The respective axis of rotation 6 is preferably formed with one plug pin in each case, which pin is in each case moulded in one piece on the inner side of one housing shell 5. In combination with the bearing receptacles in the region of the clamping members 4 and corresponding apertures (not shown in further detail) in the region of the respective oppositely-positioned housing shell 5, the through-flow regulating device according to FIGS. 4 to 15 is therefore formed by only four components, namely the two housing shells 5 and the two clamping members 4 onto which the toothing segments 11 and the wing-shaped operating levers 8 are in each case moulded.

The invention claimed is:

1. A through-flow regulating device for a hose line of a medical infusion system that, in a mounted state, is operatively connected to the hose line and is manually adjustable relative to a hose section of the hose line in order to change a fluid through-flow rate of the hose section, the through-flow regulating device comprising:

two clamping members, wherein:
  each clamping member is a cylindrical body rotationally movable about an axis of rotation, wherein the two axes of rotation of the two clamping members are parallel,
  each cylindrical body has a circumferential edge having a circumferential contour,
  the two clamping members are mounted in a rotationally movable manner wherein the hose section is extended in a longitudinal direction between the circumferential edges of the two clamping members,
  the two clamping members flank a jacket of the hose section on opposite sides with their respective circumferential edges such that the two clamping members and the longitudinal extension direction of the hose section lie in a common radial plane,
  the circumferential contour of at least a portion of at least one clamping member is formed in an eccentric manner relative to the axis of rotation of the at least one clamping member; and
a synchronizing device, wherein the two clamping members are mounted in a rotationally movable manner relative to the synchronization device such that the two clamping members move synchronously in opposite directions to one another using the synchronizing device, and wherein the synchronizing device has two circular-arc-shaped toothing sections that mesh with one another, wherein each circular-arc-shaped toothing section corresponds to a respective one of the two clamping members.

2. The through-flow regulating device according to claim 1, wherein at least one of the two clamping members includes an eccentric clamping section on the circumferential contour of the at least one clamping member, the eccentric clamping section having a curved design with a radial supporting wall region and an axial supporting wall region that act upon the hose section on a jacket side relative to an axis of rotation of the at least one clamping member in dependence on a rotation of the at least one clamping member.

3. The through-flow regulating device according to claim 2, wherein, in a circumferential direction of the at least one clamping section, a spacing of the radial supporting wall region relative to the axis of rotation of the at least one clamping member changes in a continuous manner over a length of the supporting wall region.

4. The through-flow regulating device according to claim 2, wherein, in a circumferential direction of the at least one clamping section, a spacing of the radial supporting wall region relative to the axis of rotation of the at least one clamping member changes in a discontinuous manner over a length of the supporting wall region.

5. The through-flow regulating device according to claim 1, wherein the two clamping members are each provided with eccentric clamping sections that are complementary to one another.

6. The through-flow regulating device according to claim 5, wherein each of the eccentric clamping sections are of mirror-symmetric design relative to a diagonal plane.

7. The through-flow regulating device according to claim 1, wherein the two clamping members are oriented relative to the hose section such that clamping forces of the two clamping members acting on the hose section lie in a common radial plane of both axes of rotation of the two clamping members.

8. The through-flow regulating device according to claim 1, wherein each of the two circular-arc-shaped toothing sections are oriented co-axially relative to the axis of rotation of their respective clamping member.

9. The through-flow regulating device according to claim 1, wherein each of the circular-arc-shaped toothing sections are provided in one piece on their respective clamping member.

10. The through-flow regulating device according to claim 1, wherein an adjustment angle of each of the two clamping members between an open position, in which the hose section is open for a full fluid through-flow, and a blocked position, in which the hose section is closed for no fluid through-flow, is less than or equal to 90°.

11. The through-flow regulating device according to claim 10, wherein a section angle covered by the respective circular-arc-shaped toothing section is at most 90°.

12. The through-flow regulating device according to claim 1, wherein the two clamping members are mounted and held relative to one another.

13. The through-flow regulating device according to claim 12, wherein the two clamping members are rotatably mounted in a carrier housing.

14. The through-flow regulating device according to claim 13, wherein the carrier housing comprises a base shell and a cover shell, between which the two clamping members are arranged, wherein the base shell and the cover shell are connected to one another in a region of the axes of rotation of the two clamping members.

15. The through-flow regulating device according to claim 1, wherein the two clamping members are identical.

16. A through-flow regulating device for a hose line of a medical infusion system that, in a mounted state, is operatively connected to the hose line and is manually adjustable relative to a hose section of the hose line in order to change a fluid through-flow rate of the hose section, the through-flow regulating device comprising:
two clamping members, wherein:
    each clamping member is a cylindrical body rotationally movable about an axis of rotation, wherein the two axes of rotation of the two clamping members are parallel,
    each cylindrical body has a circumferential edge having a circumferential contour,
    the two clamping members are mounted in a rotationally movable manner wherein the hose section is extended in a longitudinal direction between the circumferential edges of the two clamping members,
    the two clamping members flank a jacket of the hose section on opposite sides with their respective circumferential edges such that the two clamping members and the longitudinal extension direction of the hose section lie in a common radial plane, and
    the circumferential contour of at least a portion of at least one clamping member is formed in an eccentric manner relative to the axis of rotation of the at least one clamping member; and
wherein each clamping member has at least one operating lever that projects outwardly relative to the axis of rotation of that clamping member in a direction opposite to the eccentric clamping section.

17. The through-flow regulating device according to claim 16, wherein each clamping member has two operating levers which project in the manner of a rocker in different directions relative to the axis of rotation of the respective clamping member.

18. The through-flow regulating device according to claim 16, wherein at least a portion of the at least one operating lever projects laterally outwards beyond the carrier housing.

\* \* \* \* \*